(12) United States Patent
Birkenbach et al.

(10) Patent No.: US 8,014,848 B2
(45) Date of Patent: Sep. 6, 2011

(54) VISUALIZATION OF PROCEDURAL GUIDELINES FOR A MEDICAL PROCEDURE

(75) Inventors: Rainer Birkenbach, Aufkirchen (DE); Christoph Pedain, Munich (DE); Andreas Hartlep, Munich (DE); Raghu Raghavan, Baltimore, MD (US); Martin Brady, Phoenix, MD (US)

(73) Assignee: Brainlab AG, Feldkirchen (DE)

( * ) Notice: Subject to any disclaimer, the term of this patent is extended or adjusted under 35 U.S.C. 154(b) by 1898 days.

(21) Appl. No.: 11/115,093

(22) Filed: Apr. 26, 2005

(65) Prior Publication Data
US 2005/0267360 A1    Dec. 1, 2005

Related U.S. Application Data

(60) Provisional application No. 60/567,584, filed on May 3, 2004.

(30) Foreign Application Priority Data

Apr. 26, 2004   (EP) .................................. 04009835

(51) Int. Cl.
*A61B 5/05*    (2006.01)

(52) U.S. Cl. ......................... 600/411; 600/431; 600/432
(58) Field of Classification Search .......... 600/407–411, 600/424, 473, 476, 427–433; 606/130
See application file for complete search history.

(56) References Cited

U.S. PATENT DOCUMENTS

| | | | | |
|---|---|---|---|---|
| 6,061,587 | A * | 5/2000 | Kucharczyk et al. | 600/411 |
| 6,381,483 | B1 * | 4/2002 | Hareyama et al. | 600/407 |
| 6,813,512 | B2 | 11/2004 | Aldefeld et al. | |
| 7,505,807 | B1 * | 3/2009 | Kucharczyk et al. | 600/411 |

FOREIGN PATENT DOCUMENTS

| | | |
|---|---|---|
| EP | 1 103 229 | 5/2001 |
| EP | 1 199 031 | 4/2002 |
| EP | 1 410 758 | 4/2004 |

* cited by examiner

*Primary Examiner* — Sanjay Cattungal
(74) *Attorney, Agent, or Firm* — Renner, Otto, Boisselle & Sklar, LLP (57) ABSTRACT

The visualization of procedural guidelines for a medical procedure, in which a medical instrument is shown in an image representation of a body portion including an area in which a medical procedure is to be carried out, wherein, in the vicinity of the functional portion of the instrument, regions or locations are indicated which are of special relevance to the procedure according to established guidelines for said procedure.

17 Claims, 6 Drawing Sheets

VISUALIZATION OF PROCEDURAL GUIDELINES FOR A MEDICAL PROCEDURE

RELATED APPLICATION DATA

This application claims priority of U.S. Provisional Application No. 60/567,584 filed on May 3, 2004, which is incorporated herein by reference in its entirety.

FIELD OF THE INVENTION

The present invention relates to a method and apparatus for visualizing procedural guidelines for a medical procedure. More particularly, the present invention relates to presenting medical rules or guidelines with respect to procedures in which a medical instrument is shown in an image representation of a body portion including an area in which a medical procedure is to be carried out.

BACKGROUND OF THE INVENTION

For many medical procedures, certain rules or guidelines exist or may be established. One example is a guideline or rule determining the location on or in a patient that a tip of an instrument should be placed in order to achieve an optimum effect. Another guideline may determine locations where such an instrument is not to be placed, thereby preventing harm to the patient or undesired results.

Medical technology has developed to a point where surgeons may use so-called image-guided surgery systems (IGS), which display image representations of body portions as well as instruments in their correct positional relationship with respect to the image representations. At present, surgeons must try to keep procedural guidelines in mind while they operate in an image-guided environment.

A problem arising from this practice resides in the fact that a surgeon, while carrying out a complicated operation, may only be able to remember or take into account a few guidelines at a time. Also, the constraints given by such guidelines may be very precise, whereas a surgeon equipped with the information of the image representation may only be able to guess or approximate whether such constraints are being fulfilled at a certain moment.

As a result, a level of uncertainty may exist when following certain medical rules or guidelines. Such uncertainty, in some instances, can lead to undesired results.

SUMMARY OF THE INVENTION

The present invention provides a method and apparatus that reduces or minimizes the level of uncertainty in applying medical rules and/or guidelines. In particular, the rules or guidelines were provided to the physician automatically, for example in a visual format, thereby allowing the physician to focus on other aspects of his work.

In accordance with the invention, a method and system for visualizing procedural guidelines for a medical procedure involves displaying an anatomical image representation of an area of interest of a patient in which the medical procedure is to be carried out; displaying at least one instrument image representation of at least one instrument with the anatomical image representation; and displaying a visualization of at least one guideline associated with a functional portion of the instrument. The methodology can be embodied in a computer-implemented program that may be carried on a computer-readable medium.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

These and further features of the present invention will be apparent with reference to the following description and drawings, wherein.

DETAILED DESCRIPTION

The present invention relates to a method and apparatus for presenting medical rules or guidelines (hereinafter collectively referred to as guidelines) to a surgeon during a medical procedure. Guidelines, as used herein, refer to accepted techniques and procedures that have proven to yield favorable results or to prevent undesirable results and/or to newly developed techniques and procedures that are believed to yield favorable results or to prevent undesirable results. As will be described in more detail below, the guidelines are presented in a visual format in conjunction with images of an area of interest of a patient, e.g., a body portion of the patient and of an instrument, e.g., a catheter. The images of the area of interest may be taken prior to the medical procedure, e.g., several days before the procedure (pre-operative), or the images may be taken concurrently with the procedure (operative). The guidelines are presented along with the images on a display, e.g., the guidelines are superimposed on the images or presented with the images, thereby allowing the surgeon to quickly ascertain whether one or more guidelines are being violated.

Figure 1:
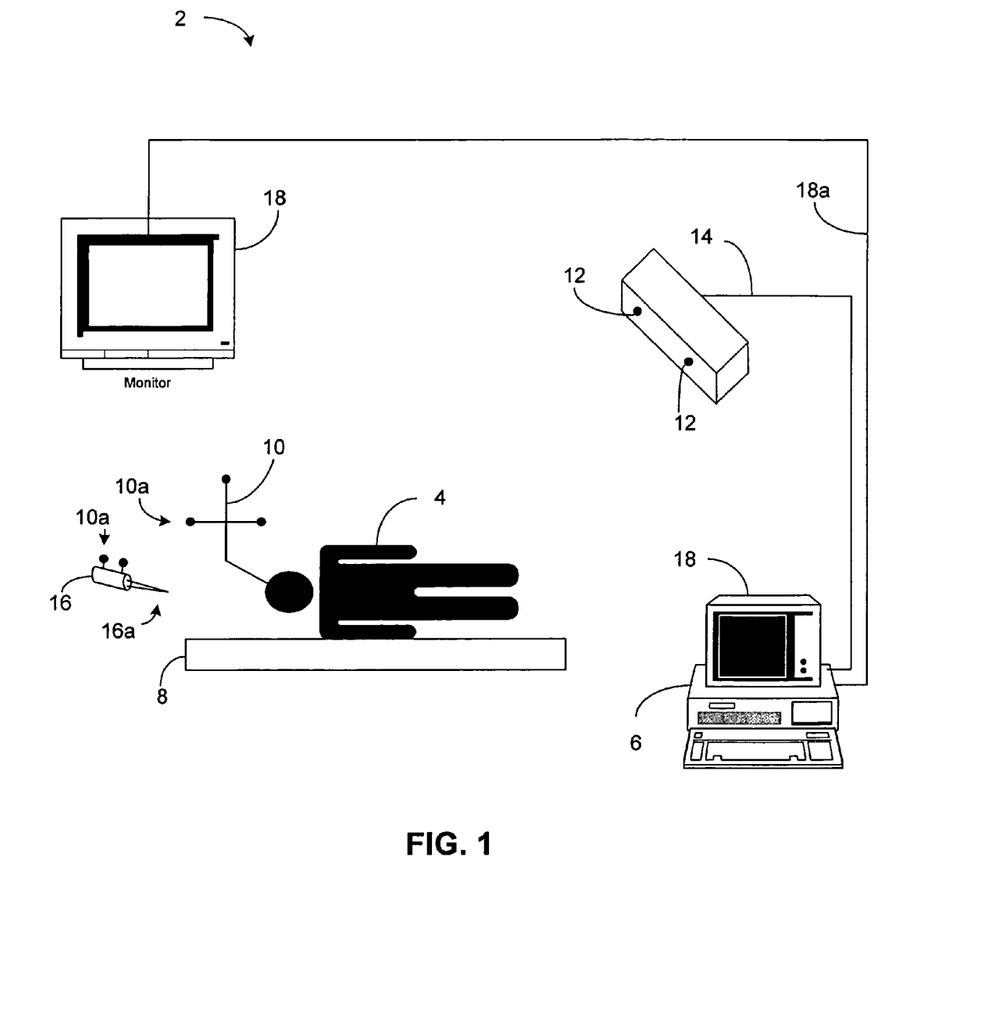
FIG. 1 is a schematic diagram of an image guided surgical system that can be used in conjunction with the present intention.

Referring to FIG. 1, an image guided surgery (IGS) system 2 that can be used in conjunction with the present invention is illustrated. IGS systems are well known in the art and therefore will not be discussed in detail herein. Briefly, pre-operative images and/or operative images of a patient 4 are provided to a computer controller 6. The patient 4 is placed on an operating table 8, and a reference star 10 is rigidly fixed to an area of interest of the patient, e.g. the cranium, spine, hip, etc. The reference star 10 includes passive or active elements 10*a* that are detectable by at least two cameras 12. The cameras 12 ascertain the spatial position of the reference star 10 and, therefore, the spatial position of the area of interest, and provide the spatial information to the computer controller 6 via a wired or wireless communications link 14.

Prior to displaying the patient's pre-operative or operative images, the patient 4 is registered into the IGS 2. Registration is the process of teaching the computer controller 6 the location of the area of interest on the patient with respect to the reference star 10. This can be done, for example, by indicating to the computer controller 6 the location of several points on the patient 4 using an instrument 16, such as a probe, for example, having active or passive emitters 10*a* thereon. Provided the computer controller 6 knows the geometry of the instrument 16, the computer controller can ascertain the location of a tip 16*a* of the instrument. By placing the tip 16*a* of the instrument on several points on the patient 4, the computer controller 6 can ascertain the spatial position of the area of interest with respect to the reference star 10 and correlate the preoperative and/or operative images to the area of interest, thereby completing registration. Once registered, the computer controller 6 displays the images on one or more displays 18 via a video link 18*a*.

As the patient 4 is moved on the table 8, the images displayed on the display 18 also move so as to always show the images with the correct positional relationship. Moreover, one or more instruments 16 used by the surgeon also can be displayed on the display 18, provided the geometry of each instrument is known by the computer controller 6. A known IGS system is VectorVision™, available from BrainLAB AG, and described, for example, in U.S. Patent Publication No. 2003/0225329, which is hereby incorporated by reference.

The vicinity of a functional portion of an instrument 16, a region or regions on or in the area of interest, and/or locations around the instrument 16 and/or the regions (hereinafter collectively referred to as "regions") may be indicated on the display 18. More specifically, regions that are of special relevance to the procedure according to established guidelines for the procedure are illustrated. The instruments and regions can be displayed in the image representation (e.g., a single image containing all information) or overlaid on the image representation (e.g., multiple images arranged one over the other), thus providing direct visual information as to whether the presently planned course of action, e.g. the presently planned trajectory of the instrument, will fulfill or violate the constraints given by the guidelines. Additionally, any level of uncertainty with respect to whether the guidelines are being accurately obeyed is reduced, since direct visual feedback of the guidelines is provided. As a result, the surgeon can concentrate on other aspects of his work. Moreover, the surgeon can rely on the visual information on the display 18 if he is not able to determine, by experience alone, whether the constraints given by the guidelines are being fulfilled.

There are, in principle, several ways of determining the regions of special relevance for a particular guideline or guidelines. For example, a fixed set of guidelines can be developed for certain medical procedures. In this case, the standard guidelines could include predetermined values that may have proven to offer good results in certain comparable procedures. Another possibility is to determine the regions of special relevance by applying guidelines computed for a current procedure on the basis of instrument and body data. While this may require a greater initial effort to achieve a basis for the visualization, it can provide better case-adapted information.

The regions of special relevance may be indicated as regions in which, according to the guidelines:
- a procedure is to be applied;
- a procedure is not to be applied;
- a procedure is preferably to be applied;
- a procedure is preferably not to be applied;
- a procedure will show an effect;
- a procedure will not show an effect;

wherein one or more of the above indications can be displayed.

The medical procedure may be the positioning of a catheter for administrating substances to an area of interest. The area of interest, for example, can be a brain portion, wherein the functional portion of the instrument is the portion of the catheter by which the substances are delivered. In such a case, the guidelines would determine regions in which:
- the delivered substance is expected to spread;
- the delivering portion of the catheter is to be placed, in order to exhibit a sufficient distance from critical tissue portions;
- the delivering portion of the catheter is to be placed, in order to exhibit a sufficient distance from other delivering portions of other catheters;

wherein one or more of the above regions may be displayed.

When fixed standard guidelines are used, such guidelines could determine that:
- the delivered substance is expected to spread in a 2 to 3 cm, in particular 2.5 cm, long substantially cylindrical area backwards from the catheter tip;
- the delivering portion of the catheter is to be placed at a distance of 5 mm to 15 mm, in particular 10 mm, from critical tissue portions, in particular such tissue portions that hinder the spread of the substance or guide the substance to undesirable locations;
- the delivering portion of the catheter is to be placed at a distance of at least 2 cm, in particular 3 cm, from other delivering portions of other catheters.

If variable guidelines are used, such guidelines may be computed on the basis of one or more of the following instrument and/or body data:
- substance flow rate;
- catheter geometry;
- tissue elasticity, e.g., how fast the tissue cuffs the catheter;
- hydraulic conductivity of the tissue, e.g., the tissue's resistance to fluid flow;

or on the basis of parameters derived from such data or measured directly, such as pressure gradient, velocity gradient or concentration gradient.

The present invention is not limited to the administration of substances by means of a catheter. Further fields of application include the following procedures:
- positioning a catheter for withdrawing substances;
- positioning a stimulation probe, e.g., an electrical stimulation probe;
- positioning a probe for gathering tissue information;
- positioning a probe for indicating a tissue location;
- positioning an instrument for withdrawing tissue, in particular a biopsy needle;
- positioning an instrument for cutting or destroying tissue, e.g., laser, ultrasound, thermal probe, etc.;
- positioning an endoscopic device.

The present invention will now be described within the context of a particular embodiment, namely, within the context of treating brain tumors by administrating a therapeutic substance via a catheter. It should be appreciated, however, that the context of treating brain tumors and/or using a catheter is merely exemplary, and the invention can be applied to other procedures and/or instruments without departing from the scope of the invention.

For the treatment of recurrent glioblastomas in the human brain, direct pharmaceutical therapies are currently under development. A prerequisite of sufficient local therapy is the capability of a therapeutic substance to reach the assigned target. Catheters, for example, are used to deliver the therapeutic substance to the target volume. The placement of the catheter is planned pre-operatively using a computerized planning system and previously acquired patient images, as well as other patient data. To avoid failure in substance delivery, certain guidelines for placing the catheter are obeyed. These guidelines are defined by the supplier of the therapeutic substance and/or by experts in the field of catheter administration.

In accordance with the present invention, the guidelines may be transformed into visualizations of certain regions in order to enable the guidelines to be displayed on the display 18. Such visualizations are "attached" or otherwise linked to a planned display trajectory of the catheter and overlaid on anatomical and/or functional patient data. Visualizing and displaying these rules, e.g. minimal depth of catheter tips or minimal distance to intra-cranial surfaces like cavities and/or sulci, enables the planning surgeon to avoid mistakes when placing the catheter.

Various physical analyses have allowed the inventors of the present invention to theoretically describe the extent of backflow of an infused fluid along a catheter track. A description of the mathematical models that were used follows. The physical parameters used in the model are listed below:

| | |
|---|---|
| K | Tissue Hydraulic Conductivity |
| G | Tissue Shear Modulus |
| φ | Extracellular Volume Fraction |
| λ | Tissue Effective Radius |
| μ | Fluid Viscosity |
| Q | Flow Rate |
| r | Catheter Radius |

In the simplest model, the tissue is assumed to be homogeneous with respect to hydraulic resistance and shear modulus, and the catheter is assumed to approximate an infinite cylinder. In this case, the backflow distance, L, is estimated using the following formula:

$$L = \frac{5}{3}\left(\frac{\pi}{120\mu}\right)^{1/5}\left(\frac{\ln(\lambda/r)}{2\pi\phi K}\right)^{4/5}\frac{Q^{3/5}r^{4/5}}{G^{3/5}} \qquad \text{Equation 1}$$

The above model provides the opportunity of adjusting the display of backflow distances according to the infusion parameters and the catheter type chosen. Computing a pressure field makes it possible to accommodate the displayed rules for nearby pressure sinks. Based on an analysis of an MRI-diffusion tensor scan, the mathematical models make it possible to take into account the varying hydraulic conductivity of tissue surrounding the catheter and to adjust the guidelines thus displayed.

Moreover, based on experiments and/or theoretical analyses, rules of thumb for the backflow distance can be derived. As an example, such rules of thumb may be summarized as in the table below:

TABLE 1

Backflow distance (mm) for various flow rates and catheter radii.

| | r = 0.5 mm | r = 0.75 mm | r = 1.0 mm | r = 1.25 mm |
|---|---|---|---|---|
| Q = 1.0 (l/minute) | 6.0 | 7.7 | 9.1 | 10.4 |
| Q = 3.0 (l/minute) | 11.7 | 14.9 | 17.7 | 20.1 |
| Q = 5.0 (l/minute) | 15.8 | 20.3 | 24.0 | 27.3 |
| Q = 7.0 (l/minute) | 19.4 | 24.8 | 29.4 | 33.4 |
| Q = 9.0 (l/minute) | 22.5 | 28.8 | 34.2 | 38.9 |

(Using parameters $K = 4 \times 10^{-8}$ cm$^4$/(dyne-sec), $G = 1 \times 10^5$ dyne/cm$^2$, = $1 \times 10^5$ cm, = $7.06 \times 10^{-3}$ g/(cm-sec).)

In one example, the backflow, based on Equation 1, can substantially fill a cylinder extending substantially backwards from the catheter tip and having a length of 2.5 cm. Given this premise, one guideline for catheter administration, for example, would be that the backflow area should substantially lie within the "white matter" tissue of the brain, preferably without contacting intra-cranial surfaces like cavities or the outer limits of the brain tissue.

Figure 2:
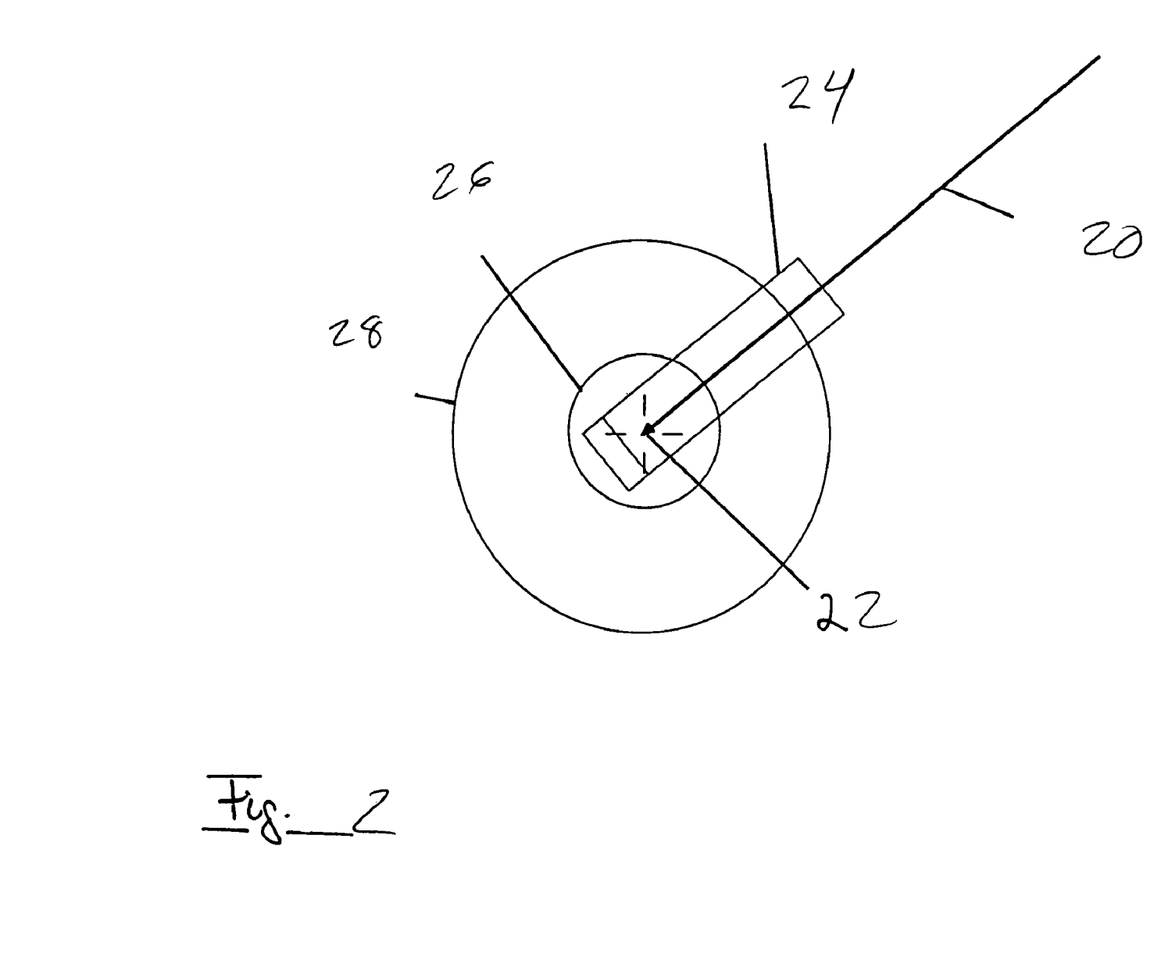
FIG. 2 is a schematic representation of an instrument, such as a catheter for administrating substances into the brain, with a visualization of certain regions surrounding a tip of the instrument that are of relevance when a substance is administered in accordance with an embodiment of the invention.

With reference to FIG. 2, a visualization of a particular set of guidelines is illustrated. The catheter has been given the reference numeral 20, and the catheter tip is indicated by a small arrow and bears the reference numeral 22. As a visualization of the above guideline, a cylinder 24 can be displayed which extends from slightly ahead of the tip 22 back towards the catheter 20, the cylinder being an elongated rectangle. Thus, the cylinder 24 represents the region where the substance is expected to spread after it has been administered and it therefore visualizes the guideline or transforms the guideline into a visualization.

Another guideline, for example, is more directly visualized by two circles 26, 28 centered on the tip 22 of the catheter 20. The first inner circle 26 may define a region around the tip 22 in which a cavity border of the brain tissue should not be located or encroached. The second outer circle 28 may define an area into which the tip of another catheter should not be placed. A surgeon, viewing on the display 18 the visualization in conjunction with the images (pre-operative and/or operative) of the area of interest, can quickly ascertain whether one or more guidelines are or may be violated.

For example, the surgeon can view the display 18, which shows the pre-operative and/or operative images of the patient along with the above visualization of the guidelines, and ascertain whether the cylinder 24 (the projected spread) is in the white matter of the brain (guideline obeyed) or partially/completely outside the white matter of the brain (guideline violated), or whether another catheter is within the second circle 28.

Figure 3:
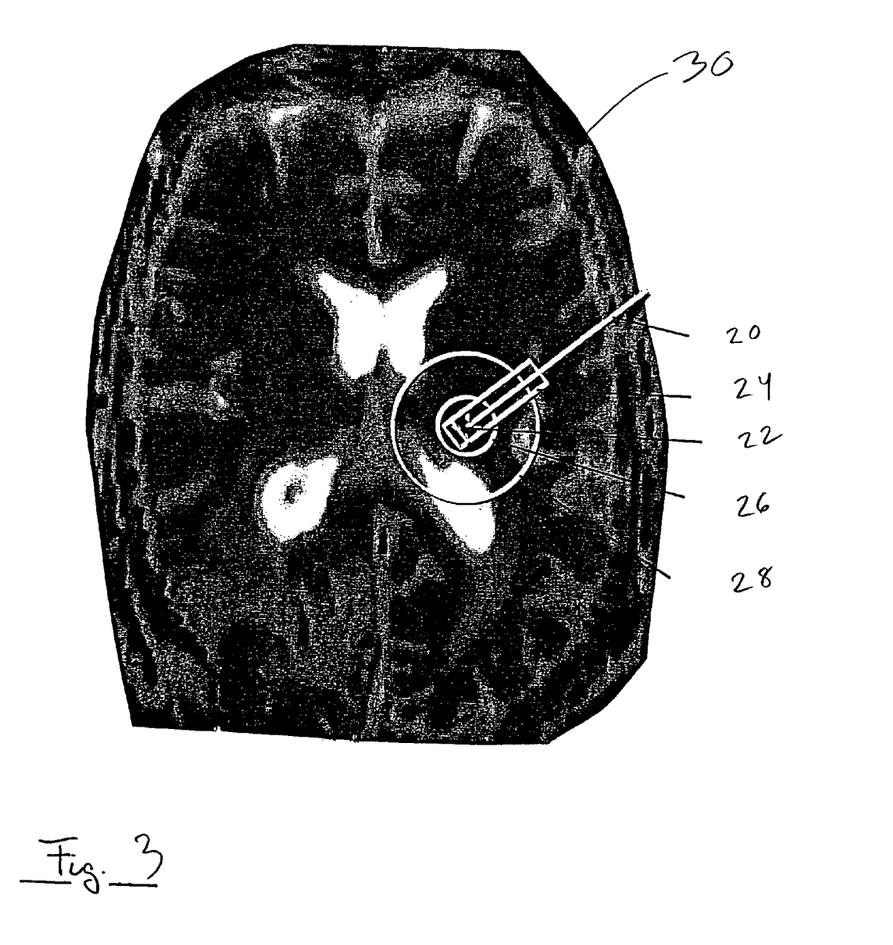
FIG. 3 illustrates the image of FIG. 1 superimposed or overlaid on an image representation of a brain area in accordance with an embodiment of the invention.
Figure 4:
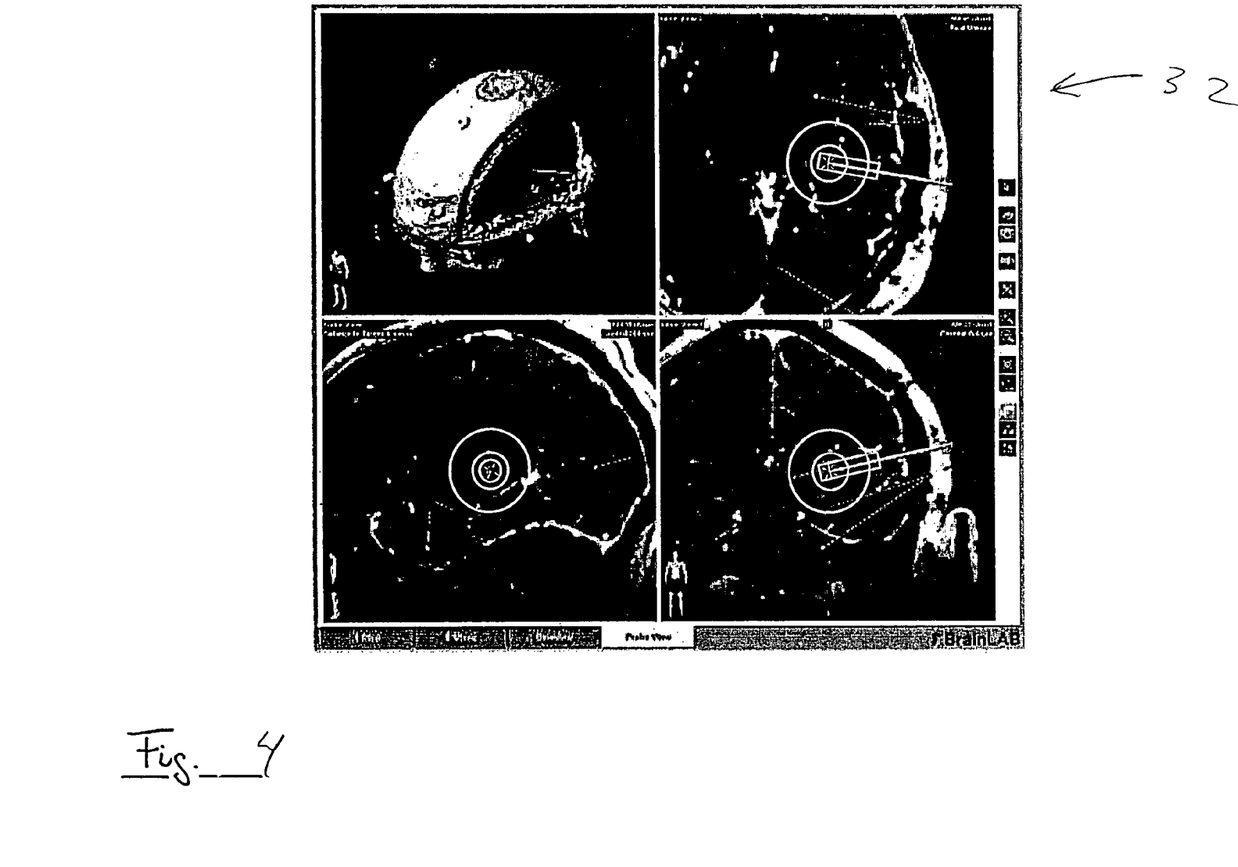
FIG. 4 illustrates three representations of the image of FIG. 3 at three different viewpoints, and one perspective representation, in accordance with an embodiment of the invention.

FIG. 3 shows such a visualization of the guidelines, e.g., a visualization of certain regions which are relevant according to the guidelines, in an MRI slice image of the skull/brain of a patient. The catheter 20, together with its tip 22, can be visibly overlaid onto the anatomical image 30 with the regions 24, 26, 28 in such a way that it becomes very easy for a surgeon to decide whether the planned catheter positioning complies with or violates the guidelines. Of course, image representations of FIG. 3 can be displayed from various angles alone or together, as well as in three dimensional perspective representations 32, as shown in FIG. 4. Such image representations allow the surgeon to quickly ascertain whether a guideline is obeyed or violated. As soon as an acceptable position for the catheter 20 has been found, e.g., a position obeying all or substantially all of the guidelines, the position can be determined as a suitable catheter placement plan.

For example, a procedure may call for multiple substances to be injected simultaneously or consecutively into the patient's brain. The surgeon can place a first catheter, which will administer the first substance, into the patient's brain according to the first guideline discussed above, and place a second catheter, which will administer the second substance, into the patient's brain according to the second guideline discussed above. Using the visualizations of the guidelines in conjunction with the IGS and the pre-operative/operative images of the patient, the surgeon can position the first catheter such that the cylinder is only in the white matter of the brain. Additionally, and again using the visualization guidelines, the surgeon can position the second catheter such that the region in the first circle 26 is not within a cavity border of the brain tissue, and the region within the second circle 28 is not within the tip of the first catheter. Accordingly, the surgeon can ascertain with reasonable certainty that the guidelines have been obeyed.

The first and second circles 26, 28 in FIG. 2 are representations of spheres having corresponding diameters and, as should be appreciated, can vary in diameter based on various factors, including the substance or substances to be injected, the amount of substance to be injected, the procedure to be performed, etc. By way of example, the inner sphere 26 may have a radius of 1 cm and the outer sphere 28 may have a radius of 3 cm. Similarly, the length of the cylinder 24 may vary as indicated by Equation 1. In the present example, the length is in the range of about 4 cm.

The invention also relates to a planning system that is able to display anatomical, functional and/or physiological patient-related image data. The system can be used to plan trajectories for the placement of intra-cranial ventricle catheters and for delivering substances into the human brain. If a trajectory is planned, then a certain catheter type and, if required, a flow rate of the infusion can be assigned to the trajectory. Since the system knows the catheter type (e.g. diameter) and the flow rate, certain guidelines for catheter placement can be displayed.

For example, the minimal depth of the catheter tip 22 can be displayed by a cylinder 24 around the trajectory. The trajectory can be displayed in the thickness of the assigned catheter type. Minimal distances between intra-cranial surfaces and the catheter tip 22 can be displayed by circles around the end of the trajectory. Distances between different catheter tips can be displayed by circles around the catheter tip having the diameter of the required distance. These visualizations can be matched onto anatomical, functional and/or physiological images of the patient.

Additionally, the guidelines can be switched on and off, and additional guidelines can be applied. The degree of importance of a particular guideline or guidelines can be indicated using different colors or shades for certain visualizations. For example, very important guidelines can be displayed in signal colors (red/yellow), whereas less important guidelines can be displayed in other colors.

Moreover, data included in the patient images can be used to determine whether a particular guideline is being fulfilled or not. In other words, the system can indicate via a visual and/or audible alarm when a particular guideline is being violated. For example, if the IGS system determines that the first circle 26 (FIGS. 2 and 3) cuts through a region identified as a cavity in the brain, the first sphere 26 is flashed on the display 18 and/or an audible alarm is issued. When the catheter is moved to an adequate position, the visual and/or audible alarm is removed, e.g., the flashing and/or sound is removed, indicating that the sphere 26 is no longer contacting a brain cavity. As should be appreciated, numerous other possible alarm conditions can be implemented depending on the guidelines for each instrument, procedure, substance, etc.

The invention further relates to an apparatus for visualizing procedural guidelines for a medical procedure. More particularly, a medical instrument can be shown in an image representation of an area of interest including an area in which a medical procedure is to be carried out. The apparatus, according to the present invention, includes a graphic processor, wherein the processor indicates on a display, in the vicinity of the functional portion of the instruments, regions of special relevance to the procedure, according to established guidelines for said procedure.

The apparatus may include an IGS 2, as illustrated in FIG. 1. The IGS 2 includes a medical tracking system, e.g., cameras 12, reference star 10 and computer controller 6, that positionally tracks one or more instruments as well as the area of interest of the patient. Additionally, the IGS includes a screen output or display 18 for displaying the visualizations of the guidelines. The IGS correlates acquired anatomical body data, e.g., pre-operative or operative image data, with the tracking information to track and display the area of interest on the display 18. Additionally, the apparatus includes software that carries out the method of the present invention. More particularly, the software presents visualizations of guidelines for medical procedures, and superimposes or overlays those guidelines with displayed area of interest to indicate whether or not a guideline is being obeyed.

The apparatus may, of course, include any device necessary for carrying out one of the features of the above-described embodiments of the method according to the present invention.

Further, the present invention includes a computer program which, when running on a computer or loaded onto a computer, carries out the inventive method, and to a data carrier comprising such a computer program.

Figure 5A:
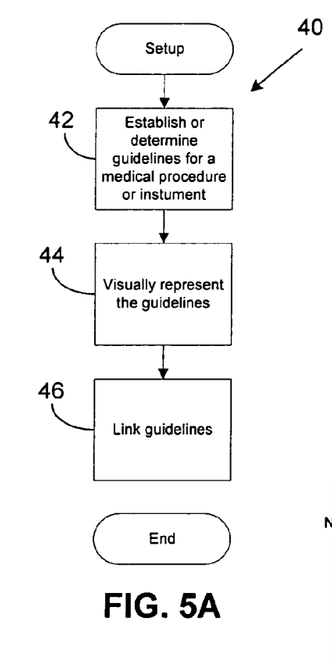
FIG. 5A is a flow diagram for setting up visualizations for guidelines in accordance with an embodiment of the present invention.
Figure 5B:
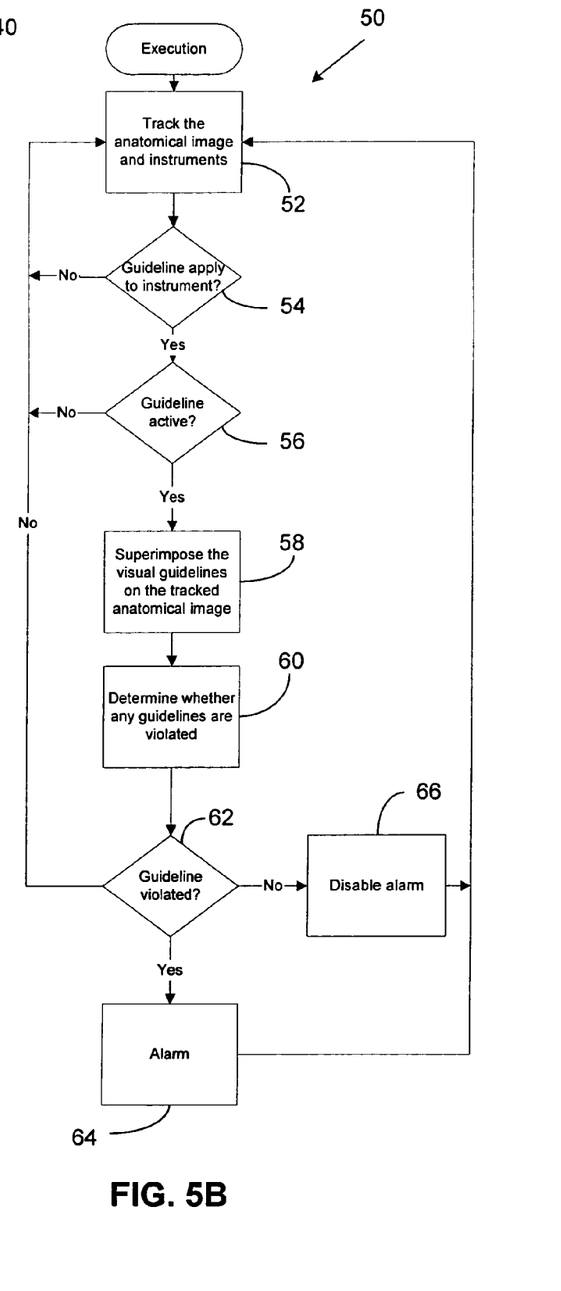
FIG. 5B is a flow diagram for presenting visualizations of guidelines in accordance with an embodiment of the present invention.

Moving now to FIGS. 5A and 5B, two flow diagrams 40, 50 illustrating the method of visually representing one or more guidelines in accordance with an embodiment of the invention. The flow diagrams include a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

FIG. 5A illustrates a setup flow chart 40 for preparing the visualizations that will be utilized in the execution flow chart 50 of FIG. 5B. Beginning at step 42, the guidelines for a particular procedure are established, provided such guidelines do not yet exist. For example, guidelines can be established based on knowledge of experts in a particular field, recommendations by a manufacturer of a device, previous experience with the procedure and/or the to substance, medical records for a particular individual or group of individuals, tests performed on a particular individual or group of individuals, etc. Alternatively, if guidelines do exist for the procedure, then the guidelines are collected or assembled.

Once the guidelines are established and/or assembled, at step 44 the guidelines are converted into visual representations or visualizations of the guidelines. This can include, for example, developing images of the respective devices, e.g., a catheter, a needle, etc., and providing colors, regions, objects, etc. to and/or around the image of the device that represent the guidelines.

For example, and as was previously discussed, circular regions can be shown around a catheter tip to indicate the status of one or more guidelines. Alternatively, the color of the device and/or the color of the regions surrounding the device can be changed based on the status of the guideline, e.g., red color indicates a violation of the guideline, while a green color indicates the guideline is obeyed.

As will be appreciated, guidelines can be represented in numerous ways, and the above examples are not intended to be limiting. Other examples include a positive (e.g., guideline obeyed) or negative (e.g., guideline violated) indication on the display, audible alerts, flashing displays, animated displays, etc. While any attribute of the image can be changed to signify that the guideline is being obeyed or violated, it is preferable that the attribute reasonably communicate to a viewer whether the guideline is obeyed or violated.

At step 46, the visualizations of the guidelines are linked to or otherwise associated with a respective instrument 16, substance and/or procedure. This association can be stored in a database of the computer controller 6, for example, for retrieval during the execution of the method.

Moving now to the execution flow chart 50 of FIG. 5B, application of the method in accordance with an embodiment of the invention will be described. It is noted that in the following description, it is assumed that pre-operative images of the area of interest of the patient have been taken, and the area of interest has been registered with the navigation system of the IGS 2.

Beginning at step 52, the area of interest is tracked by the navigation system of the IGS 2. Pre-operative and operative images of the area of interest can be viewed on the display 18. Additionally, any instrument having markers 10a also is tracked by the navigation system and can be viewed on the display 18.

At step 54, it is determined whether any of the instruments 16 currently being tracked by the navigation system are associated with a guideline. As is known in the art, navigation systems can distinguish one instrument from another based on the placement of the markers 10a on each instrument. Each type of instrument has a marker placement that is unique from a different type of instrument, e.g., a probe would have different marker placement than a drill, but two identical probes would have the same marker placement. By identifying the instrument, it can be ascertained whether the particular instrument has an associated guideline. If the instrument is not associated with a guideline, then the method moves back to step 52 and continues tracking the area of interest and the instruments. If, on the other hand, a guideline is associated with the particular instrument, then the method moves to step 56.

At step 56, it is determined whether the guideline for the particular instrument is active or inactive. Guidelines can be activated or deactivated by the surgeon for various reasons. If the guideline has been deactivated (inactive), then the method moves back to step 52 and continues tracking the area of interest and the instruments. If the guideline is activated (active), then the method moves to step 58.

At step 58, the visualization of the guideline for the particular instrument is retrieved and superimposed or overlaid on the pre-operative/operative images of the area of interest, such that the visualization of the guideline follows or otherwise tracks the movement of the instrument. Moreover, the pre-operative/operative images, the instrument, and the visual guidelines all can be viewed simultaneously, thereby providing direct visual feedback as to whether a guideline is being obeyed or violated as an instrument is positioned in the area of interest.

For example, a guideline for the injection of a particular substance may be that the substance should only be injected into the white matter of the brain. As was described previously, this guideline can be visually represented by a cylinder 24 starting just beyond the tip 22 of the catheter 20 and extending back a predetermined distance. The surgeon, viewing the visualization of the guideline and the anatomical image 30 on the display 18, can manipulate the catheter 20 such that the cylinder 24 lies within the white matter of the anatomical image 30 of the brain, thereby obeying the guideline, as indicated at step 60.

Alternatively, the computer controller 6 of the IGS 2 can determine whether the guideline is being violated based predetermined criteria. For example, if the guideline states that a second catheter should not be within a predetermined distance of a first catheter, and this guideline is represented visually by a circle 28 around the tip 22 of the first catheter 20, then, in order to accurately display the circle 28, the computer controller 6 must know or be able to ascertain the radius of the circle 28. Since the navigation system is operated by the computer controller 6, the computer controller is aware of the location of other instruments 16 in the area of interest. Should another catheter be placed with the predetermined distance of the first catheter, the computer controller can determine that this is in violation of the guideline.

At step 62, it is determined whether the guideline is violated, e.g., by the surgeon or by the computer controller. If the guideline is violated, then at step 64 the surgeon, either by perceiving the violation on the display 18 or by an alarm generated by the computer controller 6, is aware of the violation. If the guideline is not violated, the alarm, if previously activated, is disabled. In both cases, the method moves back to step 52 and continues tracking.

Accordingly, by converting guidelines into visualizations and representing those visualizations in the context of image guided surgery, the level of uncertainty with respect to whether a guideline is obeyed or violated is reduced. Moreover, the surgeon is not burdened with focusing on what guidelines apply to a particular procedure, substance, tool, etc., as those guidelines can be visually presented to him, thereby allowing him to focus on other aspects of his work.

Figure 6:
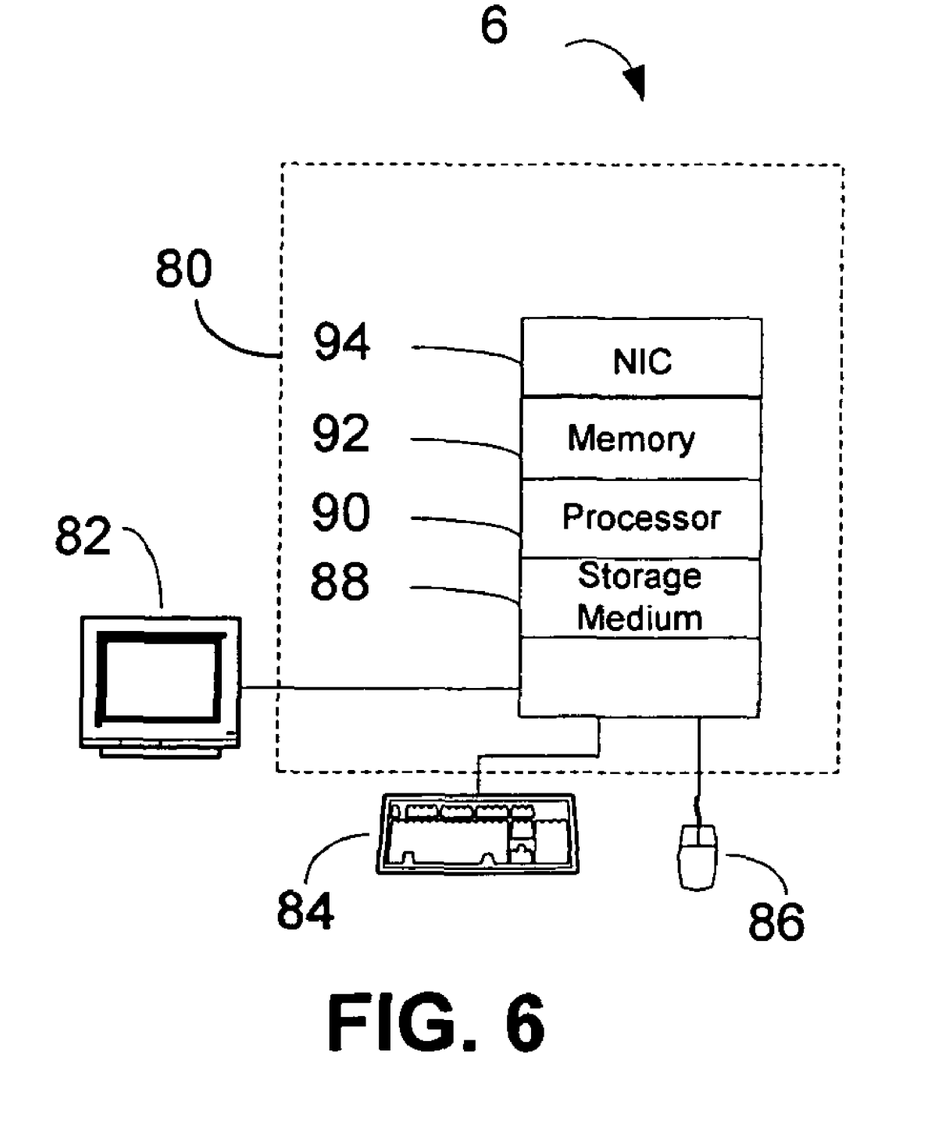
FIG. 6 is a block diagram of a computer system that can be used to implement the method of the present invention.

Moving to FIG. 6, a computer controller 6 for executing a computer program in accordance with the present invention is illustrated. The computer controller 6 includes a computer 80 for processing data, and a display 82 for viewing system information. The technology used in the display is not critical and may be any type currently available, such as a flat panel liquid crystal display (LCD) or a cathode ray tube (CRT) display, or any display subsequently developed. A keyboard 84 and pointing device 86 may be used for data entry, data display, screen navigation, etc. The keyboard 84 and pointing device 86 may be separate from the computer 80 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 84 and pointing device 86. A touch screen is well known by those skilled in the art and will not be described in detail herein. Briefly, a touch screen implements a thin transparent membrane over the viewing area of the display 82. Touching the viewing area sends a signal to the computer 80 indicative of the location touched on the screen. The computer 80 may equate the signal in a manner equivalent to a pointing device and act accordingly.

For example, an object on the display 82 may be designated in software as having a particular function (e.g., view a different screen). Touching the object may have the same effect as directing the pointing device 86 over the object and selecting the object with the pointing device, e.g., by clicking a mouse. Touch screens may be beneficial when the available space for a keyboard 84 and/or a pointing device 86 is limited.

Included in the computer 82 is a storage medium 88 for storing information, such as application data, screen information, programs, etc. The storage medium 88 may be a hard drive, for example. A processor 90, such as an AMD Athlon 64™ processor or an Intel Pentium IV® processor, combined with a memory 92 and the storage medium 88 execute programs to perform various functions, such as data entry, numerical calculations, screen display, system setup, etc. A network interface card (NIC) 104 allows the computer 80 to communicate with devices external to the computer controller 6.

The actual code for performing the functions described herein can be easily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for visualizing procedural guidelines for positioning a catheter for for administration of a substance to a body portion of a patient, comprising the steps of:
    displaying an image representation of the body portion including an area in which the administration is to be carried out;
    displaying in the image representation of the body portion an image representation of a delivering portion of the catheter;
    indicating in the image representation prior to administration of the substance, in the vicinity of the delivering portion of the catheter, regions or locations which are of particular relevance to the administration according to at least one established guideline for the administration, the established guideline being selected from a group of established guidelines that respectively determine regions or locations in which
    the delivered substance is expected to spread,
    the delivering portion of the catheter is to be placed in order to afford a sufficient distance from critical tissue portions, and
    the delivering portion of the catheter is to be placed in order to afford a sufficient distance from other delivering portions of other catheters.

2. The method of claim 1, wherein the guidelines are fixed standard guidelines, determining that:
    the delivered substance is expected to spread in a 2 to 3 cm long, substantially cylindrical area backwards from the catheter tip;
    the delivering portion of the catheter is to be placed at a distance of 5 mm to 15 mm from tissue portions that hinder the spread of the substance being administered or guide the substance to undesirable locations;
    the delivering portion of the catheter is to be placed at a distance of at least 2 cm from the delivering portions of any other catheter being used.

3. The method of claim 1, wherein the regions or locations of particular relevance are determined by application of fixed standard guidelines.

4. The method of claim 1, wherein the regions or locations of particular relevance are indicated as regions or locations in which, according to one or more of the guidelines:
    an administration is to be applied,
    an administration is not to be applied,
    an administration is preferably to be applied,
    an administration is preferably not to be applied,
    an administration will show an effect, and
    an administration will not show an effect.

5. The method of claim 1, wherein the step of using a fixed guideline related to the expected spread is given by $$L = \frac{5}{3}\left(\frac{\pi}{120\mu}\right)^{1/5}\left(\frac{\ln(\lambda/r)}{2\pi\phi K}\right)^{4/5}\frac{Q^{3/5}r^{4/5}}{G^{3/5}}$$

where L is the back flow distance, K is the tissue hydraulic conductivity, G is the tissue shear modulus, $\phi$ is the extracellular volume fraction, $\lambda$ is the tissue effective radius, $\mu$ is the fluid viscosity, Q is the flow rate and r is the catheter radius.

6. The method of claim 1, wherein the step of displaying the anatomical image representation of an area of interest of the patient includes displaying at least one three-dimensional perspective representation of the anatomical image.

7. The method of claim 1, further comprising the step of enabling or disabling each guideline or adding additional guidelines.

8. A program embodied in a non-transitory computer-readable medium for visualizing procedural guidelines for a medical procedure, comprising:
    code that carries out the method of claim 1.

9. The method of claim 1, further comprising the steps of:
    positionally tracking the catheter and body portion with a medical tracking system; and
    correlating acquired anatomical body data with the tracking information.

10. The method of claim 9, wherein the step of correlating acquired anatomical body data with tracking information includes using an image-guided surgery system to perform the correlation, and the anatomical and catheter image representations are a screen output of the image-guided surgery system.

11. The method of claim 1, wherein regions or locations of particular relevance are determined by applying guidelines that are computed for a current procedure on the basis of the catheter and body data.

12. The method of claim 11, wherein the guidelines are variable guidelines that are computed on the basis of at least one of the following catheter or body data:

substance flow rate, catheter geometry, tissue elasticity, and hydraulic conductivity of the tissue, or on the basis of parameters derived from such data or measured directly.

13. The method of claim 12, wherein the variable guidelines are computed on the basis of parameters derived or measured directly from catheter or patient data, including at least one of a pressure gradient, a velocity gradient, and a concentration gradient.

14. The method of claim 1, further comprising the step of adding at least one of visual and audible attributes to the visualization of the guidelines.

15. The method of claim 14, wherein the step of adding visual attributes includes the step of adding at least one of colors, animation, textual information, and flashing to the visualizations to represent whether the guidelines are being obeyed or violated.

16. A system for visualizing procedural guidelines for positioning a catheter for a for administration of a substance to a body portion of a patient, comprising:

a processor circuit having a processor and a memory;

a visualization system stored in the memory and executable by the processor, the visualization system comprising:

logic that displays an image representation of the body portion including an area in which the administration is to be carried out;

logic that displays in the image representation of the body portion an image representation of a delivering portion of the catheter;

logic that indicates in the image representation, in the vicinity of the delivering portion of the catheter, regions or locations which are of particular relevance to the administration according to at least one established guideline for the administration, the established guideline being selected from a group of established guidelines that respectively determine regions or locations in which the delivered substance is expected to spread, the delivering portion of the catheter is to be placed in order to afford a sufficient distance from critical tissue portions, and the delivering portion of the catheter is to be placed in order to afford a sufficient distance from other delivering portions of other catheters.

17. The system of claim 16, further comprising:

logic that positionally tracks the catheter and the area of interest with a medical tracking system; and logic that correlates acquired anatomical body data with the tracking information.

* * * * *